US007335168B2

(12) United States Patent
Rugg (10) Patent No.: US 7,335,168 B2
(45) Date of Patent: Feb. 26, 2008

(54) MONITORING SYSTEM FOR ANIMAL HUSBANDRY

(75) Inventor: Geoffrey B. Rugg, Boulder, CO (US)

(73) Assignee: Bio Equidae, LLC, Boulder, CO (US)

( * ) Notice: Subject to any disclaimer, the term of this patent is extended or adjusted under 35 U.S.C. 154(b) by 210 days.

(21) Appl. No.: 11/198,914

(22) Filed: Aug. 5, 2005

(65) Prior Publication Data
US 2006/0155172 A1    Jul. 13, 2006

Related U.S. Application Data

(60) Provisional application No. 60/599,133, filed on Aug. 5, 2004.

(51) Int. Cl.
| A61B 5/103 | (2006.01) |
| A61B 5/117 | (2006.01) |
| A61B 5/00 | (2006.01) |
| A61B 5/04 | (2006.01) |
| G01L 5/16 | (2006.01) |
| A01K 37/00 | (2006.01) |
| A62B 35/00 | (2006.01) |

(52) U.S. Cl. ............... 600/595; 600/587; 600/300; 600/301; 600/372; 600/382; 600/383; 600/384; 600/391; 73/865.4; 128/920; 119/712; 119/859

(58) Field of Classification Search ........ 600/587, 600/595, 300, 301, 372, 382, 383, 384, 391; 73/865.4; 128/920; 119/712, 859
See application file for complete search history.

(56) References Cited

U.S. PATENT DOCUMENTS 6,113,539 A * 9/2000 Ridenour ............ 600/300
6,532,901 B2 * 3/2003 Isley et al. ............ 119/712
6,536,377 B2 * 3/2003 Beaver ............ 119/859

(Continued)

FOREIGN PATENT DOCUMENTS

DE    10130558 A1 *    3/2003

OTHER PUBLICATIONS

Kai et al., "Use of an instrument sandwiched between the hoof and shoe to measure vertical ground reaction forces and three-dimensional acceleration at the walk, trot, and canter in horses," American Journal of Veterinary Research, Aug. 2000, vol. 61, No. 8, American Veterinary Medical Association.

(Continued)

*Primary Examiner*—Max F. Hindenburg
*Assistant Examiner*—Jeffrey G Hoekstra
(74) *Attorney, Agent, or Firm*—Marsh Fischmann & Breyfogle LLP (57) ABSTRACT

A monitoring system (800) is operative for receiving sensor signals and analyzing the sensor signals to identify events or conditions of interest, such as colic, with respect to a monitored animal. The sensors may be animal-borne sensors such as motion related sensors. The system (800) includes a processor (802) operative to identify the conditions of interest based on a stored pattern database (806), threshold tables (808) and heuristic engines (812). Upon identification of a condition of interest, a human expert may be consulted and alerts may be generated as required.

1 Claim, 7 Drawing Sheets

U.S. PATENT DOCUMENTS

| | | | |
|---|---|---|---|
| 6,706,002 B1* | 3/2004 | Halleck et al. | 600/586 |
| 2001/0050062 A1* | 12/2001 | Isley et al. | 119/712 |
| 2002/0010390 A1* | 1/2002 | Guice et al. | 600/300 |
| 2002/0016529 A1* | 2/2002 | Iliff | 600/300 |
| 2002/0092480 A1* | 7/2002 | Beaver | 119/859 |
| 2002/0095073 A1* | 7/2002 | Jacobs et al. | 600/300 |

OTHER PUBLICATIONS

Ratzlaff et al., "Relationships between hoof-acceleration patterns of galloping horses and dynamic properties of the track," American Journal of Veterinary Research, Apr. 2005, vol. 66, No. 4, American Veterinary Medical Assocation.

Pratt, G.W., "Model for injury to the foreleg of the Thoroughbred racehorse," Equine Veterinary Journal, 1997, pp. 30-32, Suppl. 23.

Gustas et al., "Relationships between fore- and hindlimb ground reaction force and hoof deceleration patterns in trotting horses," Equine Veterinary Journal, 2004, pp. 737-742, vol. 36, No. 8.

Barrey et al., "Locomotion evaluation for racing in Thoroughbreds," Equine Veterinary Journal, 2001, pp. 99-103, Suppl. 33.

Gustas et al., "In vivo transmission of impact shock waves in the distal forelimb of the horse," Equine Veterinary Journal, 2001, pp. 11-15, Suppl. 33.

Leleu et al., "Analysis of trotter gait on the track by accelerometry and image analysis," Equine Exercise Physiology 6, 2002, pp. 344-348, Suppl. 34.

Keegan et al., "Evaluation of a sensor-based system of motion analysis for detection and quantification of forelimb and hind limb lamenss in horses," American Journal of Veterinary Research, May 2004, vol. 65, No. 5, American Veterinary Medical Association.

Dyhre-Poulsen et al., "Equine hoof function investigated by pressure transducers inside the hoof and accelerometers mounted on the first phalanx," Equine Veterinary Journal, 1994, pp. 362-366, vol. 26, No. 5.

Clayton, Hilary M., "Instrumentation and techniques in locomotion and lameness," Equine Practice, Aug. 1996, pp. 337-350, vol. 12, No. 2, Veterinary Clinics of North America.

\* cited by examiner

MONITORING SYSTEM FOR ANIMAL HUSBANDRY

CROSS REFERENCE TO RELATED APPLICATION

This application claims priority under 35 U.S.C. § 119 to U.S. Provisional Application No. 60/599,133 entitled: "Animal Monitoring System" and having a filing date of Aug. 5, 2004, the contents of which are incorporated by reference herein.

FIELD OF THE INVENTION

The present invention is directed to automated monitoring of animals. More specifically, the present invention is directed to monitoring symptoms or indications such as characteristic movements or other behaviors or medical parameters of animals to detect events/conditions of interest.

BACKGROUND

In animal husbandry settings, for example equine boarding facilities, breeding facilities, zoos and dairy farms, the health of animals is typically monitored by the staff of the facility and/or the owners of the animals. Such monitoring typically involves periodically visually inspecting the animals to identify any outward signs of potentially disabling conditions or other events of interest. As will be appreciated, many potentially disabling or fatal conditions are treatable and early detection may reduce the impact of the condition on a particular animal and/or prevent/reduce the spread of a contagious condition to other animals. Such events of interest may include, without limitation, equine colic, foaling, injury and lameness. It will be appreciated that many other examples are possible.

In equine settings, one potentially fatal condition of particular interest is colic. The term "colic" is applied to a variety of conditions of the digestive tract of which pain is the chief symptom. Various malfunctions, displacements, twistings, swellings, infections, or lesions of this complex body system are recognized as colic. The most common types of colic include, without limitation, intestinal impaction, colon impaction, intestinal obstruction, colon obstruction, intestinal strangulation, displacement, volvulus, spasmodic, gas, ileus, enteritis/colitis, and gastric distention/rupture. Less common types of colic include intestinal and colon parasitic colics, gastric ulcers, and intestinal stasis.

The causes of the various different types of colics are often unknown and may be linked to factors including the confinement of grazing animals for substantial periods of time each day. Colic is one of the oldest known disorders of horses, and has long been considered to be the most dangerous and the most costly equine internal disease. In this regard, colic is believed to be the leading cause of preventable death in horses and is generally considered to be responsible for about 17.5% of all equine deaths. Colic can kill a horse in a matter of hours and thus early detection is paramount. Detected in time, colic can usually be treated successfully using, for example, various non-invasive treatments, (e.g., drug treatments) as well as invasive (e.g., surgical) techniques. While this discussion has focused on colic for purposes of illustration, it will be appreciated that it may be desired to monitor performance, working, show or other horses for a variety of injuries and other medical conditions, to accumulate medical data, or to detect a variety of non-medical events of interest such as escapes from containment, environmental exposures and the like.

In dairy settings, one particular concern is lameness. That is, foot and leg problems are major animal health concern for many dairy farmers. Typically lameness results in poor performance and can result in substantial economic loss. For instance, when a dairy cow begins to favor a particular leg/foot, it may be an indication that the cow's hooves need to be trimmed to prevent worsening of the condition. Left untreated, initial lameness may result in one or more conditions that may require antibiotic treatment. For instance, an inflammation within the hoof may develop into a condition of laminitis, which may further cause mastitis. Economically, the result of lameness is typically much greater than the treatment costs alone. In this regard, it will be appreciated that treatment may reduce milk yields, require milk to be discarded during antibiotic treatment, and of course require additional labor costs. Accordingly, it is desirable to identify lameness early such that corrective measures may be taken before antibiotic treatment is required. Again, dairy cows may be monitored for many other reasons. Also, it will be appreciated that it may be desired to monitor a variety of animals in a variety of settings.

As noted above, in animal husbandry settings, monitoring the health of animals typically involves visually inspecting the animals to identify any outward signs of potentially disabling conditions or other events of interest. However, in many cases animals are only monitored during routine care (e.g., feeding) of the animals and, perhaps, at the end of the day. In such instances, many animals may be present at a single time and careful monitoring of individual animals may be difficult. Furthermore, such monitoring may be performed by inexperienced and/or poorly trained individuals. Finally, and perhaps most importantly, many animals in animal husbandry settings are left unmonitored for long periods of time (e.g., overnight) during which the onset of a condition of interest may occur. In particular, most colic deaths occur at night. As a result, conditions of interest may be identified too late to save the animal or only after the condition has worsened or treatment options have narrowed.

Some systems have been proposed or implemented for monitoring animals. For example, certain stall based or other external sensor systems have been proposed or implemented to detect conditions such as foaling based on sensing certain behaviors. Other systems attempt to provide a foaling alert based on sensing the expulsion of a foal or water. Still other sensing systems have been used in experimental or training environments to monitor an animal's gait. Additionally, a variety of sensors have been used in clinical and experimental settings to monitor various medical parameters to detect conditions of interest.

However, such systems are generally subject to one or more of the following limitations: 1) they are limited to monitoring an animal in a particular location, e.g., in a stall or otherwise in proximity to a sensor; 2) they are limited to monitoring a specific parameter or medical condition; 3) they are intended for brief experimental or periodic monitoring use and thus have limited potential for identifying sudden onset conditions; 4) they are intended for supervised or attended operation; 5) they entail a significant risk of entanglement or animal injury; 6) they are not conveniently transportable as may be desired; and/or 7) they are not intended as mass market systems or are otherwise cost prohibitive. It will be appreciated that medical and other conditions may be better monitored and greater animal information may be collected and aggregated by using a system that can be widely deployed by owners or others, that can be safely utilized in a variety of locations and environments, including overnight or longer term environments, to provide a variety of information for analysis, and that can make information available for remote analysis and aggregation.

SUMMARY OF THE INVENTION

The inventors have recognized that by detecting the motion, sound, temperature, pulse rate, respiratory rate and/or sweating or other discharges of an animal utilizing one or more sensors, the onset of numerous conditions of interest may be detected utilizing an automated system. Outputs from one or more such sensors may be collected and compared to known baselines for a particular animal and/or compared to known baselines for a particular type and/or breed of animal. Upon identifying a change or pattern in the output of the sensors that is indicative of one or more conditions of interest, an output may be generated to alert a caregiver of a potential event of interest. Accordingly, a caregiver may then inspect and/or treat the animal.

In this regard, the present invention is directed to a method and apparatus ("utility") for monitoring an animal for a condition of interest. The invention enables such monitoring to detect medical and non-medical events of interest or to obtain or aggregate information regarding animal behaviors and conditions. In this regard, the invention allows for safe and reliable long-term monitoring of animals in a variety of conditions including in the animals' customary living environments, whether in stalls or outside. Significantly, the invention allows for identification of events that may require prompt attention as well as remote notification of caregivers. In this manner, the invention can be used to save animals, improve diagnosis, minimize the potential harmful consequences of various conditions, enhance treatment options, reduce lost revenues, and increase caregiver peace of mind.

In accordance with one aspect of the present invention, a utility is provided for monitoring a non-human animal for a condition of interest. For example, the non-human animal may be a working animal, a performance animal, a show animal, a pet, an exotic animal or other animal. The condition of interest may be a medical condition such as colic, injury or lameness, or a non-medical condition such as an escape or undesired environmental exposure. Significantly, the animal may be monitored on a long-term basis to identify a sudden onset condition of interest potentially requiring prompt attention.

The utility involves attaching a sensor to the animal, receiving an output from the sensor that is potentially indicative of the condition of interest, processing the output to obtain processed information regarding the condition of interest, and providing an output related to the condition of interest. At least one of the steps of receiving the sensor signal and providing an output involves a wireless transmission of data between a first transfer node at the animal and a second node separate from the animal. For example, the wireless transmission may be an RF, Infrared, microwave or other transmission. The type of transmission employed in this regard may depend on power requirements, potential interferences, licensing issues and performance in challenging environments (through water, mud, etc.)

A variety of architectures may be used to implement this aspect of the invention. For example, the sensor output may be digitized, filtered, analyzed, or otherwise processed by local processing resources at the animal or such processing may be separately implemented. In the latter regard, such processing may be executed locally, for example, at a stable, barn or other caregiver facility or may be executed remotely, e.g., via transmission of data across a wide area network such as the Internet. It will thus be appreciated that the system may be implemented as a fully contained system within the control of a caregiver, a hosted application in the control of an application provider or other service provider, or a combination thereof. Different revenue models may be associated with such differing architectures.

In addition, a variety of different types of sensors may be employed in accordance with this aspect of the invention depending, for example, on the nature of the monitoring application. In this regard, the animal based sensors may be internal (e.g., implantable) or external sensors. Some examples of animal based sensors that may be employed include motion/rate sensors, force/strain acoustic sensors, temperature sensors, electrical sensors (e.g., for electrocardiography, pain detection, electrointestineography, etc.), liquid sensors (e.g., for detecting liquids associated with foaling, or sampling sweat, urine or other liquids), gas sensors (e.g., for analyzing breath, gaseous emissions, etc.) and optical sensors (such as oximeter sensors, motion sensors and cameras).

Similarly, the processing of the signal may vary depending on a number of factors including the particular monitoring application involved. Generally, such processing may involve filtering to distinguish the signal of interest from artifact, pattern matching and threshold analyses. For example, in the case of detecting colic, motion sensors may be employed to sense motions indicative of colic such as stretching of the abdomen, looking at the flanks, persistent pacing and pawing at the ground. Such motion related indicators may be identified based on analysis of the detector signal to identify associated signal characteristics. This may involve pattern matching, one or more threshold analyses or a variety of other time-based, frequency-based, or other domain analyses. Such analyses may implement fixed algorithms or may be adaptive or heuristic in nature. Additionally, associated thresholds and other values may be theoretically or empirically derived. Moreover, continuing with the colic example, other factors may be of interest such as the presence or absence of sweating, urination, etc. Such other factors may be detected by other kinds of sensors such as fluid sensors or acoustic sensors that may be animal based or non-animal based. In the latter regard, such sensors may be configured for sensing the microenvironment (e.g., the stall, trailer or other local environment) of the animal or the macroenvironment (e.g., weather environment) of the animal. Accordingly, the processing may involve a multivariant analysis including inputs from multiple types of animal based sensors or from animal based and non-animal based sensors.

Different types of outputs may be provided again depending, among other things, on the particular application. One significant class of applications involves detecting medical or other events requiring prompt attention. In this case, an alarm or other notification may be provided. Such a notification may be provided locally and may be in any suitable form such as visual, audible or the like. Additionally or alternatively, such an output may be provided remotely, e.g., via a wireless or wire line voice, data, and/or other network. In other cases, the output may be physiological parameter or behavior information which can be aggregated for medical research or scientific analysis.

In accordance with another aspect of the present invention, a utility is provided for monitoring a horse via an animal-borne sensor to identify a colic related event. The utility involves providing at least one horse-borne sensor for generating a sensor signal potentially indicative of the colic related event, operating the sensor to provide the sensor signal and outputting data based on the sensor signal to a processor operative for identifying the colic related event based, at least in part, on the sensor signal. One or more sensors of the same or multiple types may be utilized in this regard. For example, multiple sensors may be utilized to provide multiple motion related signals. In one embodiment, such sensors are attached to each of the horse's hooves and to the horse's head. Additional sensors such as acoustic sensors may be utilized.

The sensor signal may be provided on an occasional or substantially continuous basis. For example, the sensor output may be provided continuously over a monitoring period, e.g., overnight, between riding or exercise sessions, or on a longer term basis. Alternatively, the sensor may be operated occasionally, for example, to conserve an associated battery or reduce use of another power source. In the case of occasional operation, such operation may occur on a prescheduled or regular (periodic) basis, or may be triggered by a defined event such as sensed motion (e.g., sensed by the sensor or a separate motion detector that may be hardwired, not battery dependent). The signal may be output in substantially raw form or may be processed prior to transmission. The output preferably involves a wireless transmission so as to avoid the need for wire line connections to the horse. The associated connection may be bi-directional to provide instructions to the animal-borne system, e.g., to initiate or cease measurements, to switch transmission modes, etc. An associated apparatus includes a sensor, attached to the horse, for providing a sensor signal potentially indicative of the colic related event and an interface for outputting the sensor signal to a processor operative for identifying the colic related event based, at least in part, on the sensor signal.

In accordance with another aspect of the present invention, a further utility is provided for monitoring a horse via an animal-borne sensor to identify a colic related event. The utility involves receiving a signal from a horse-borne sensor where the signal is potentially indicative of a colic related event and analyzing the sensor signal to identify the colic related event. For example, the step of receiving may involve detecting a wireless signal and/or receiving an output from an antenna. The signal may be analyzed to identify a pattern associated with colic or to compare a calculated value to a predetermined colic threshold. A single parameter or a multi-variant analysis may be applied in this regard. In addition, such analysis may involve time domain, frequency domain or other domain processing of the signal.

According to another aspect of the present invention, the utility is provided for monitoring an animal (e.g., horse, cow, exotic animal, etc.) to identify an event of interest based on a motion related parameter. For example, the event of interest may be a medical or non-medical event requiring prompt attention. More specifically, the inventor has recognized that many conditions of interest in animal husbandry settings may be characterized at least in part by movements of the animal. For instance, the state of colic may be characterized by an abrupt change in normal behavior in which various degrees of restlessness are seen. Mild colic may produce behavior such as: the stretching of the abdomen, looking at the flanks, repeated yawning and/or teeth grinding. Signs of moderate colic may include: persistent pacing in the stall; pawing at the ground; kicking at the belly; adopting a crouching stance; grunting, and getting up and down frequently. Severe colic signs may include the above, but with profuse sweating, rolling and occasionally self-inflicted trauma. Likewise, the state of lameness is typically characterized by a change in the normal gait of an animal. In either case, the symptoms of one or more conditions of interest may involve motions or behavior of the animal and/or associated sounds.

The utility involves attaching a sensor to the animal for sensing the motion related parameter, operating the sensor to provide a sensor signal and analyzing the sensor signal to identify the event of interest. For example, the sensor may provide position information or rate information, e.g., velocity (or simply speed) or acceleration information. In this regard, the sensor may include an accelerometer and/or a gyroscope. Such information may be provided relative to multiple spatial axes. The sensor signal may be analyzed to identify any of various events of interest such as a colic event, an injury, foaling, lameness or other conditions that may be identified based on the motion related parameter. An associated apparatus includes a sensor, attached to the animal, for sensing a motion related parameter, a processor for analyzing data based on the sensor signal to identify the event of interest and interface structure disposed between the sensor and the processor. Novel structure and methodology are provided with respect to each of the sensor side and a processor side functionality.

According to a further aspect of the present invention, a utility is provided for affixing a sensor to the hoof of a hoofed animal. It will be appreciated, in this regard, that affixing a sensor to a hoof is particularly challenging due to the physiology of the hoof as well as the rugged environment of the hoof. In the latter regard, a sensor attached to a hoof may be subjected to scratching or other contact by the animal or other animals as well as exposure to mud, snow or other environmental factors. The utility involves providing the sensor, and adhesively bonding the sensor to the animal's hoof, e.g., using a horseshoe adhesive. In this regard, the sensor may be directly adhered to the hoof or may be bonded to the hoof by way of separate support structure. Preferably, such a separate support structure allows access, for example, to change a battery or service an associated component while the adhesive bond remains intact. The utility may further involve a mechanical attachment to the hoof, such as a screw attachment, to supplement the adhesive connection. An associated apparatus includes a sensor for sensing a hoof related parameter and an adhesive for bonding the sensor to the hoof.

According to a still further aspect of the present invention, a utility is provided for monitoring multiple animals, for example, in a communal setting, to identify conditions of interest. The utility involves attaching at least one sensor to each of the animals, providing a processing platform operative for processing sensor signals to identify conditions of interest and linking the sensors attached to the multiple animals to the processing platform. In one implementation, the sensors are linked to the processing platform via a wireless connection and the signals are encoded in a manner that enables distinguishing the signals from the different animals. In this manner, certain efficiencies are provided in relation to the processing. For example, a single processing platform can support monitoring multiple animals and difficulties associated with updates to the processing logic are minimized. The processing platform may be locally controlled or may be interconnected to the sensors via a wide area network such as the Internet.

BRIEF DESCRIPTION OF THE DRAWINGS

For a more complete understanding of the present invention and further advantages thereof, reference is now made to the following detailed description taken in conjunction with the drawings, in which.

DETAILED DESCRIPTION

Reference will now be made to the accompanying drawings, which assist in illustrating the various pertinent features of the present invention. Although the invention will now be discussed primarily in conjunction with equine applications, and in particular to the detection of colic, it should be expressly understood that the invention is applicable to other applications. For instance, the invention may be applied to other animals such as cattle as well as exotic animals (e.g., zoo animals) for the purpose of detecting estrus, birthing, lameness, as well as other conditions such as injury. Additionally, certain aspects of the invention are useful in gathering and aggregating various information, for example, regarding animal behavior, health and physiology, for medical, scientific or other purposes. In this regard, the following description of an equine monitoring system is presented for purposes of illustration and is not intended to limit the invention to the form or applications disclosed herein. Consequently, variations and modifications consummate with the following teachings, and skill and knowledge of the relevant art, are within the scope of the present invention. The embodiments described herein are further intended to explain modes known of practicing the invention and to enable others skilled in the art to utilize the invention in such, or other embodiments and with various modifications required by the particular applications for uses of the invention.

The description set forth herein is separated into four subsections. Initially, an overview of the animal monitoring system is provided. An individual animal monitoring system is then disclosed with particular application to detecting colic events. Thereafter, a multiple animal monitoring system is set forth in the context of the present invention. Finally, individual components of the animal monitoring system are set forth in detail.

System Overview

Figure 1:
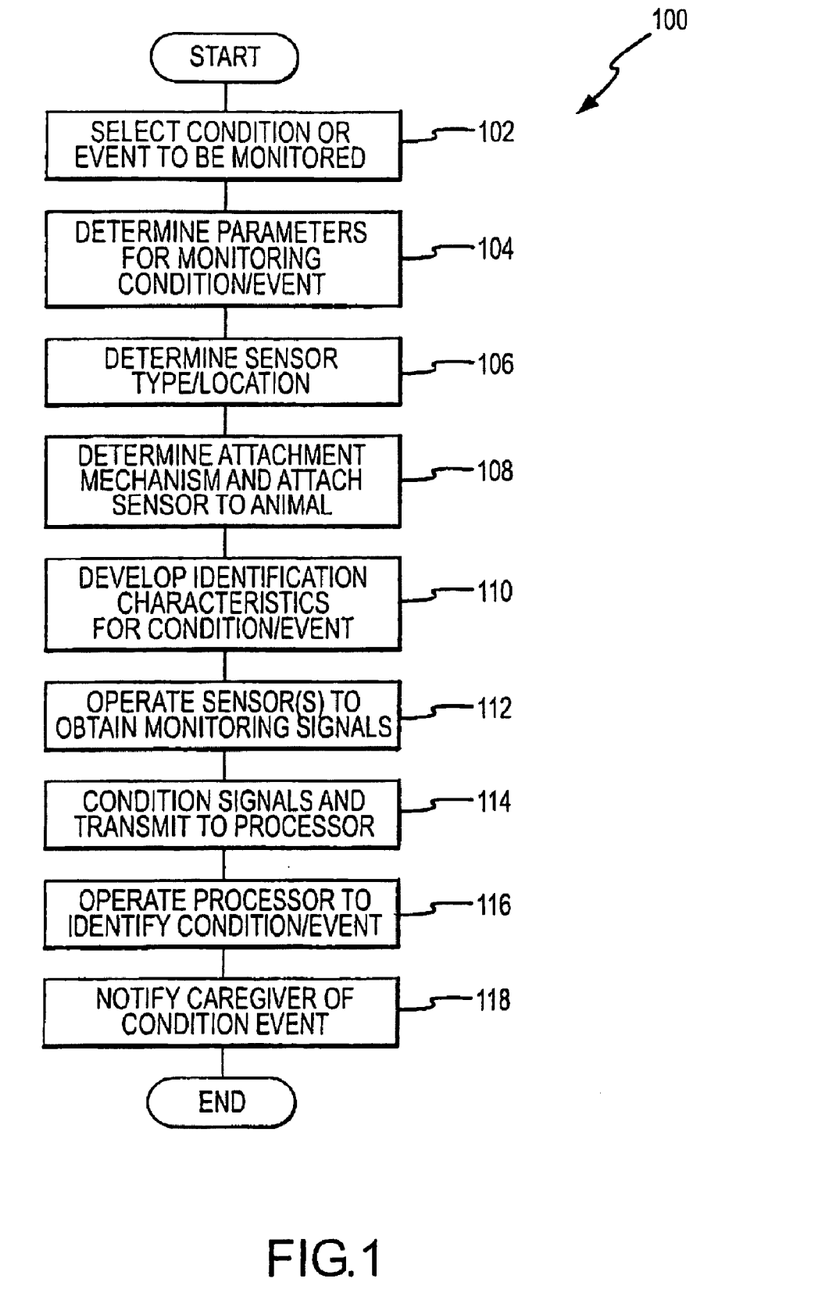
FIG. 1 is a flow chart illustrating an animal monitoring process in accordance with the present invention.

FIG. 1 is a flow chart providing an overview of the animal monitoring system of the present invention. As discussed above, the system can be used to monitor a variety of conditions or events with respect to animals under analysis. Accordingly, the process 100 of FIG. 1 is initiated by selecting (102) the condition or event to be monitored. These may relate to behavior, physiological conditions or other conditions such as escape or exposure potentially harmful environmental conditions. Thus, the system of the present invention may be used to monitor health conditions, e.g., for which early intervention is of value, to provide supplemental data post discovery, to provide supplemental data pre-discovery (e.g., that may become of value once an event/condition is known), for educational value to equine professionals or owners, or for emotional value (e.g., to monitor animals while at work, on vacation, etc.).

With regard to medical conditions, it is presently expected that the system is useful to monitor at least the following conditions in horses:

Acute and Chronic Laminitis
Acute Serous Arthritis
Bacterial Septicemia
Bruised Sole
Bucked Shins
Cast in Stall
Cervical Injury
Chronic Backpain
Colic and other alimentary digestive and gastrointestinal problems
Cracked Hoof Wall
Crypt. Parvum
DOD/OCD
EIA
EMND
Equine protozoal myeloencephalitis (EPM)
Foal Pneumonia
Fracture
Knee-Knocking
Longtoe Foot
Nail Bind
Navicular Disease
OPD (Heaves)
Osselets
Osteoarthritis and joint disease
Osteochondrosis
Pricked Foot
Respiratory disease-misc
Rhodococcus equi
Salmonella
Sheared And Contracted Heels
Spinal Ataxia
Splints
Tendonitis
Tom Hoof Laminae
Tying Up
Vesicular Stomatitis
Wobbler syndrome and these conditions in cows:

Lameness
Coliform (acute) mastitis
Respiratory problems, including BRD, BRD Complex, pneumonia and pasteurellosis
Digesting problems, including bloat, scours, acidosis, and displaced abomasums
Poisoning
Neurological diseases
Calving
Detection and tracking of heat (estrus)
Milk fever
Grass tetany
Blackleg Enterotoxaemia
Clostridal enteritis
Botulism, ketosis, fat cow syndrome, redwater disease, and vesicular stomatits
Foot and Mouth Disease (FMD)
Bovine Spongiform Encephalopathy (BSE) "Mad Cow Disease"
Contagious bovine pleuropneumonia (CBPP)
Rinderpest
Rift Valley Fever Although a number of horse and cow conditions have been specifically identified, it will be appreciated that other conditions may be monitored in horses and cows, and these or other conditions may be monitored in other animals in accordance with the present invention.

In addition, this system can be used to identify conditions or events related to animal performance. It is noted in this regard that performance animals are athletes. These animals are trained to achieve high levels of performance. However, they can not provide feedback to their trainers. The system of the present invention can be used in this regard to provide information regarding a variety of parameters. Moreover, these parameters can be provided over long time periods and in actual performance conditions rather than being limited to treadmill acquisition or the like. Among the parameters that can be monitored in this regard are:

Ventilation Analysis
Heart Rate Zones
Blood Gas Analysis
Body Temperature
Cardiac Output
Stride Biometrics
Gas Exchange
Blood Lactic Acid Concentration
Mixed Venous Blood Gas Analysis
Blood Pressure
Sweating Rate
Conformation The present invention can also be used to monitor conditions or events of interest relating to the microenvironment or mnacroenvironment of the animal under analysis. With regard to the microenvironment, a variety of conditions for which early intervention is of value may be detected such as fire, dust or the like. With regard to the macro environment, sudden barometric or temperature change, or a variety of other weather or other conditions can be detected. It will be appreciated that data may also be collected using the system of the present invention for research, scientific or other medical purposes, including purposes unrelated to any predetermined condition or event of interest.

In the illustrated process 100, after a condition or event to be monitored has been selected, parameters are determined (104) for monitoring the condition or event. For example, in the case of detecting colic events, it has been recognized that such events may be identified based on certain motion related parameters. For example it has been observed that the onset of a colic event may be identified based on characteristic movement such as persistent pacing in the stall, pawing at the ground, kicking at the belly, adopting a crouching stance, grunting, and getting up and down frequently. This suggests that motion related parameters may be monitored. Similarly, certain animal movements may characterize pre-birth stages of foaling such as restlessness, tail switching, pacing and the like. Additionally, colic, foaling and other conditions may be indicated by other parameters such as sweating, increased heart rate, increased respiration rate, pain, fluid discharges and the like. Accordingly, a variety of parameters may be of interest depending on the selected condition or event.

Once the parameters to be monitored have been determined, one or more appropriate sensor types and locations may be determined (106). For example, in the case of colic, motion sensors may be disposed on the hooves and the head to detect the noted colic related movements. Electrodes, acoustic sensors (e.g., for sensing heart rate, urination, or the presence or absence of gut sounds), optical sensors (e.g., oximeter sensors or cameras), liquid sensors (e.g., for blood analysis to implement temperature sensing, adrenaline for pain identification, glucose, or gene expression or for other body fluid analysis with respect to conductivity, dissolved gas, dissolved solids, ions, pH, viscosity, tubidity or the like) or other sensors may be disposed at appropriate locations on the animal under analysis to detect other conditions.

The illustrated process 100 then proceeds by determining (108) an attachment mechanism in attaching the sensor to the animal. It will be appreciated that the attachment mechanism will generally depend on the sensing application and attachment location. For example, in the case of attaching sensors to a hoof, adhesives and mechanical attachment mechanisms may be used as described below. In the case of attaching a sensor to a horse's head, it may be preferred to attach the sensor using a breakaway halter or the like. Electrodes may be attached using adhesives and it may be necessary to prepare the sensor location by removing hair, cleaning the location or the like.

Identification characteristics are also developed (110) for the condition/event of interest. This may occur prior to and/or after the initiation of the analysis. In this regard, some of the relevant characteristics may be known a priori. For example, in the case of colic, it may be known that it is desired to detect behaviors such as looking at the flanks and pawing at the ground and certain signal properties corresponding to these movements may be characterized. However, it may also be useful to distinguish such signals from normal activities for the individual animal under consideration. Accordingly, patterns associated with normal activities (e.g., baseline data) and patterns associated with conditions of interest may be developed heuristically. More generally, the present invention can be used to obtain a large volume of data which can be analyzed to identify patterns of interest and distinguish such patterns from other signals.

The sensor or sensors can then be operated (112) to obtain monitoring signals. In this regard, the sensors may operate continuously during an extended monitoring period or may be operated from time-to-time, e.g., periodically or in response to a triggering event as discussed above. The signals may then be conditioned (114) and transmitted to a processor. Such conditioning may involve analog-to-digital conversion, filtering, and preliminary processing. It will be appreciated that the processing may be distributed between animal-borne resources and a remote processor. With regard to transmitting data, such transmissions preferably involve a wireless interface between the horse and a remote platform and vice versa so as to avoid wire line connections with attendant entanglement concerns and other damage concerns (e.g., due to rodents). It will be appreciated that the signals may be transmitted to a local or remote processor. In this regard, the present invention lends itself to telemedicine applications. Indeed, the invention may be used to enable rapid consulting with experts across town or around the world. It is expected that it may be useful to have human involvement in identifying or confirming certain conditions of interest, e.g., prior to generating an alert. In the case of multi-animal monitoring environments, for example, at stables or other boarding facilities, identification information may be encoded into the transmissions to enable signals from different animals to be distinguished. For example, such encoding may involve multiplexing schemes such as frequency division multiplexing, time division multiplexing or code division multiplexing or may otherwise involve appending of code information to the transmitted signals.

The processor is then operated (116) to identify the condition or event. This may involve pattern matching, threshold comparisons or the like. In addition, this may involve a single variable analysis or multi-variant analysis, e.g., involving motion sensor information and acoustic sensor information. When a condition/event of interest is identified, the caregiver can be notified (118). For example, this may be accomplished by way of an audible or visual alarm, or by way of a telephony or data network.

Individual Animal Motion Monitoring System

Figure 2:
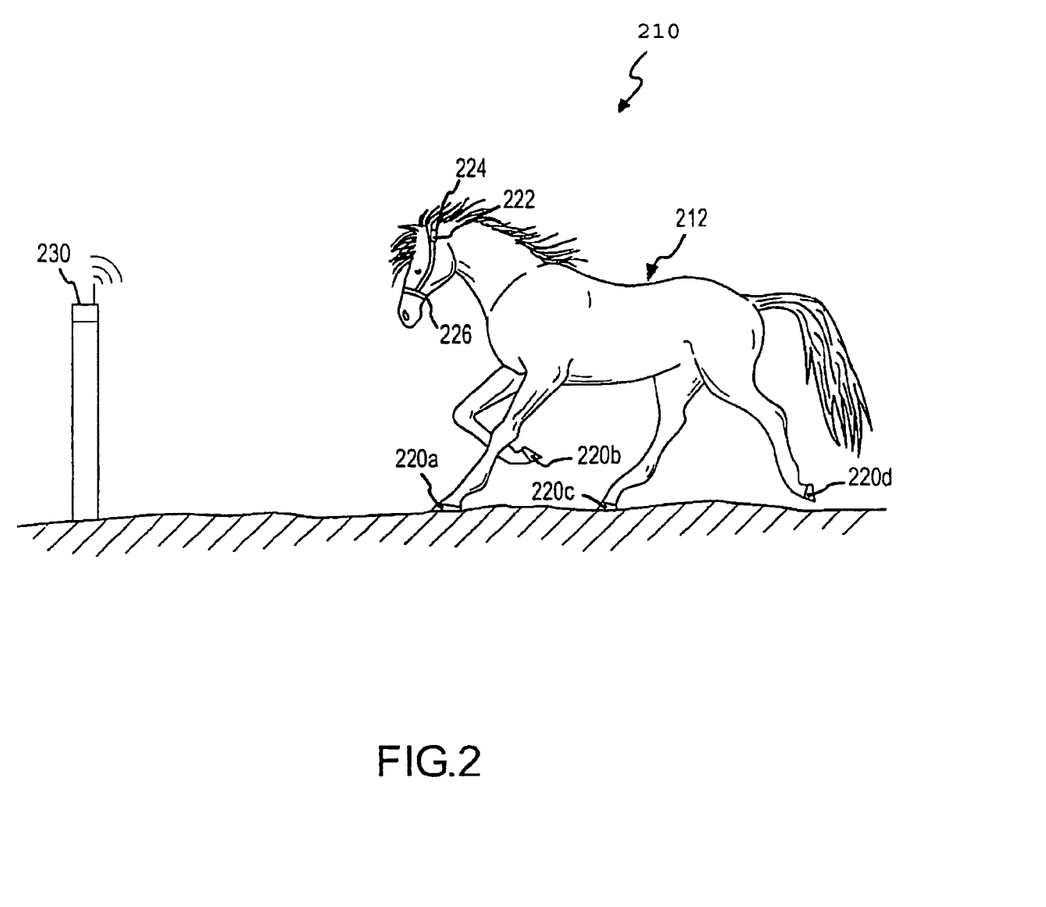
FIG. 2 is a schematic diagram illustrating an animal monitoring system for monitoring a single animal in accordance with the present invention.
Figure 3:
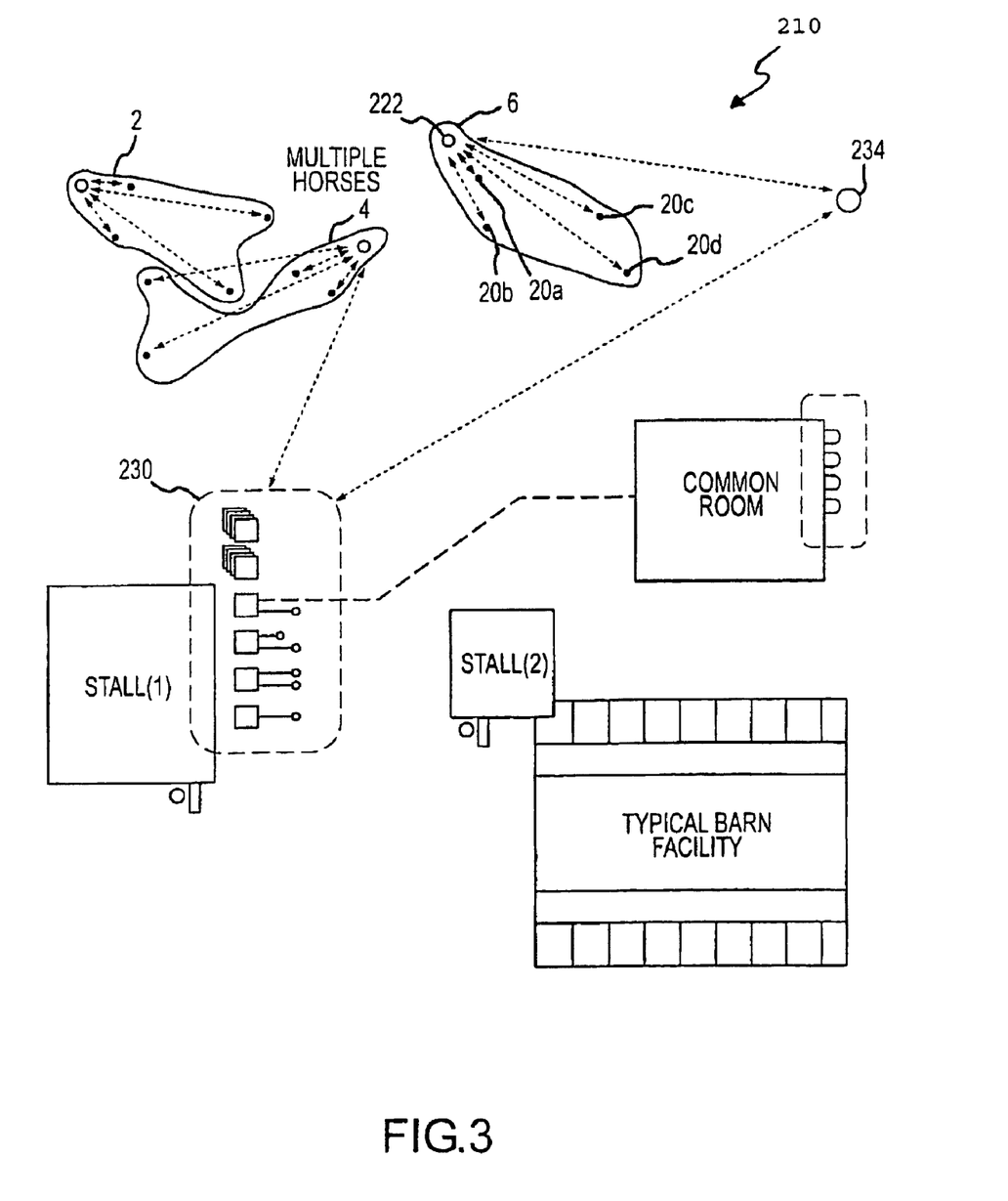
FIG. 3 is a schematic diagram illustrating an animal monitoring system for monitoring multiple animals in accordance with the present invention.

FIGS. 2 and 3 illustrate an animal motion monitoring system 210 as utilized on a horse 212. As shown, the motion monitoring system includes a plurality of sensors that are attached to the horse 212. Specifically, in the embodiment shown, four sensors are interconnected to the hooves of the horse 212. These hoof sensors 220a-d include at least a motion sensor that is operative to detect movement of each leg/hoof of the horse 212. Interconnected to the head of the horse is a head sensor 222. The head sensor 222 is also operative to detect motion of the horse's head. In the embodiment shown, the head sensor 222 is incorporated into a transceiver module 224. However, it will be appreciated that the head sensor and transceiver module 224 may be separate units. The transceiver module 224 is able to communicate with each of the hoof mounted sensors 220a-d as well as the head sensor 222. Furthermore, the transceiver module 224 is operative to transmit data from the sensors 220a-d, 222 to a remote computer for analysis purposes, as will be discussed herein.

In the illustrated embodiment, sensors 220a-d and 222 may include, for example, an accelerometer and/or inertial gyro sensor. Use of sensors located on each hoof as well as the head of the horse 212 allows the system 210 to track the motions of the horse's legs and head for comparison with known patterns, which may include normal patterns as well as events of interest patterns. That is, by monitoring the output of each sensor 220a-d and 222, the relative positions of the sensors may be determined and correlated to animal posture or movement.

The hoof sensors 220a-d may be interconnected to the horse's hooves in any appropriate manner. For instance, the sensors may be glued to an outside surface of the hoof and/or utilize a shallow penetration screw that extends into a portion of the hoof. In any case, it will be appreciated that as the hoof grows out, the sensor 220a-d will have to be removed and repositioned higher on the hoof. This may need to be done about as often as the horse is re-shoed. Another option to maintain the hoof sensors 220 in contact with the hooves and/or legs of the horse is to mount the sensors in a hoof boot or legging. Preferably, when utilized with a boot/legging, the hoof sensors 220 will be held in direct contact with a surface of the leg and/or hoof of the horse. This direct contact may allow for improved motion detection as well as the detection of additional physiological parameters (e.g., temperature) as will be more fully discussed herein. In any case, hoof sensors 220a-d are operative to generate a motion signal indicative of movement of the horse's leg. This motion signal may be transmitted over a wireless link between each hoof sensor 220a-d and the transceiver module 224.

In the embodiment shown, the transceiver module 224 is mounted to the head of the horse 212. However, it will be appreciated that components of the transceiver module 224 may be mounted to other portions of the horse 212. However, in the illustrated embodiment, a sensor 222 is mounted to the head of the horse such that the position or movement of the horse's head may be determined. Generally, the transceiver module 224 will serve two functions: 1) tracking the head and hoof motion and 2) relaying hoof and head motion data to a remote computer 230. In an alternate embodiment, the transceiver module 224 may also process sensor data to identify the onset of one or more events of interest. However, in the present embodiment, the remote computer 230 is utilized to reduce the size and power requirements of the transceiver module 224.

As shown, transceiver module 224 and the head sensor 222 are mounted to the head of the horse utilizing a breakaway halter 226. However, it will be appreciated that any means of mounting a sensor to the head of the horse may be utilized including the use of an implantable motion sensor. However, such implantable sensors will require onboard power sources such as, for example, kinetic energy sources and/or a battery.

Remote computer 230 may be any hardware module that is operative to receive and process sensor data. Preferably, the size of the remote computer may be reduced to allow the remote computer 230 to be removed from a first location (e.g., barn) and taken with the horse to another location during travel. In this regard, it may desirable that the remote computer 230 be able to fully function using alternate power sources (e.g., AC sources and DC sources).

Alternatively, the remote computer may be accessed during travel via a WAN. In any case, the remote computer 230 is operative to receive and process sensor data to identify changes in animal behavior relative to known baseline behaviors. Once a difference is detected that corresponds with an event of interest, the remote computer 230 is operative to generate an output. Such an output may be a local output (e.g., a light and/or sound) or may be an output that is adapted for delivery over a communications network. In this regard, the remote computer 230 may include an output port (e.g., hardwired or wireless) that is adapted to provide the output to one or more communications networks. Such communications networks may include, without limitation, telephony networks (wireless and/or land line), the Internet and/or a VPN. The output may be in any appropriate form based on the communications network utilized. For instance, such output may be a text, voice and/or other data output. Additionally, the remote computer 230 may be operative to provide a local output such as an audible or visual alarm. In any case, the output indicating a potential event of interest may be delivered to a predetermined caregiver such that appropriate action may be taken.

One function of the remote computer 230 is to utilize the motion sensor data received from the transceiver module 224 to determine how the horse is moving and behaving. Accordingly, the remote computer 230 utilizes pattern recognition algorithms, threshold comparisons or other techniques. Generally, remote computer 230 analyzes/compares movements of the horse 212 against known developed movement criteria. By monitoring the output from the hoof sensors 220a-d and the head sensor 222, the relative positions of these sensors 220a-d and 222 may be determined. In this regard, the general posture of the horse 212 and its movements may be determined at any given time. Accordingly, repetitive movements associated with the pain of colic may be identified by comparing the monitored motions against known 'colic movements'. These movements/patterns may include colic patterns where, for instance, the horse 212 is looking and/or kicking at its belly region. In one arrangement, upon repeating a number of known colic movements a predetermined number of times over a given time period, an alarm may be generated. That is, the remote computer 230 may generate an output that may be sent to the caregiver.

FIG. 3 illustrates a network in which multiple horses may be monitored utilizing a single monitoring system having a plurality of separate horse mounted sensor sets. In the embodiment shown, three separate sensor sets 2, 4, 6 are utilized to allow for monitoring three different horses. Each sensor set 2, 4, 6, includes four hoof mounted sensors 220a-d a head sensor 222 which in the embodiment shown is included in a transceiver module 224 as discussed above in relation to FIG. 2. Outputs from each of the sensor sets are again received by a remote computer 230. Alternatively and/or additionally, a relay transceiver unit 234 may be utilized for large acreage facilities. Likewise, two or more such relay transceiver units 234 may be utilized if necessary. In the present embodiment, the remote computer 230 is operative to receive signals from the three sensor sets and continuously monitor outputs from each sensor set against known patterns.

In order to separate signals from different sensor sets, the remote computer 230 and sensor sets may incorporate any appropriate technology. For instance, each sensor set may utilize a separate frequency or, the sensor set may be assigned a predetermined code. In the latter regard, code division multiplexing may be utilized to separate sensor data from separate sensor sets at a common frequency. In any case, the remote computer 230 is operative to receive and compare movement data associated with the sensor sets against normal patterns.

In one particular embodiment, the multiple horse monitoring system 210 may be utilized in a barn facility to allow for monitoring multiple horses maintained in the facility. In a further embodiment, the system may utilize one or more remotely operated cameras to allow for remote viewing of, for example, individual stalls within the facility. As will be appreciated, the monitoring system may be of particular use at night when nobody is located at the facility. Incorporation of cameras to viewing each stall within the facility may allow a caregiver to receive a critical event signal and remotely view the animal associated with the critical event to make a determination whether or not that animal requires immediate assistance. In one arrangement, such cameras are accessible over an Internet connection. To facilitate use of such remote cameras, automated lighting systems may be provided for each stall and/or the entire facility. Alternatively, night vision cameras may be utilized.

Individual Monitoring System Components

Figure 4:
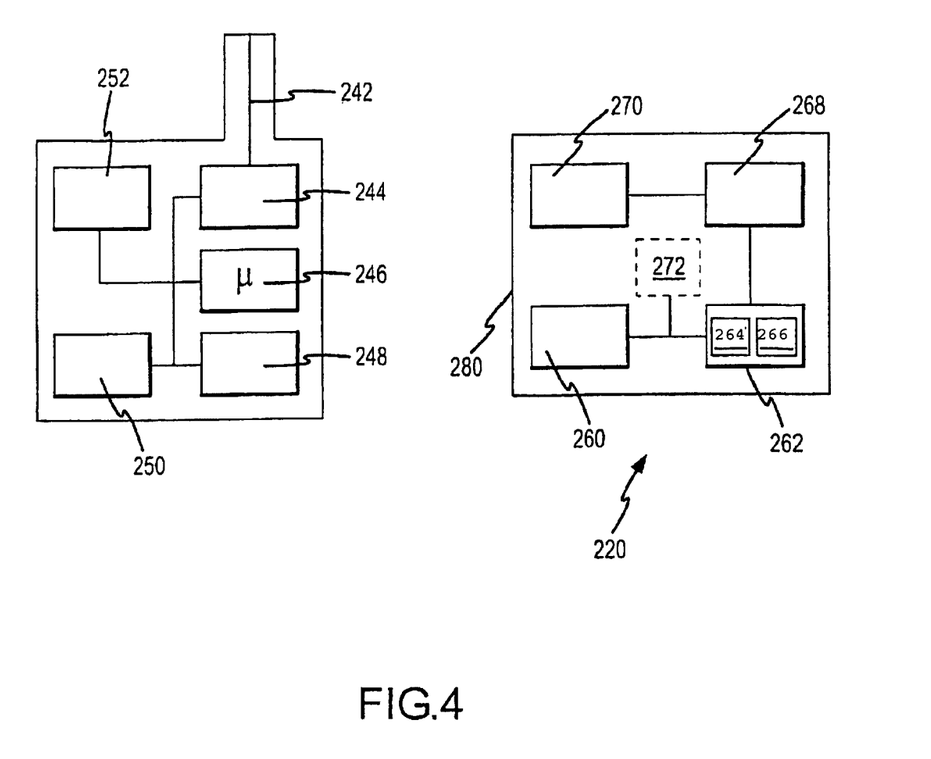
FIG. 4 is a schematic diagram of an animal monitoring system in accordance with the present invention.

The transceiver module 224 is operative to send and receive signals to and from each of the sensors 220-a-d and 222. In this regard, the transceiver module 224 includes an antenna 242 interconnected to a transceiver 244 for transmitting and receiving signals; a microprocessor 246; a memory 248 for storing data and/or operating instructions; a power source 250 (e.g., rechargeable battery); and optionally a user display 252. In further embodiments, the transceiver module 224 may also include a user input such as, for example, a keypad and/or an infrared reader. In any configuration, the transceiver module 224 is able to receive wireless data outputs from the sensors 220a-d and 222 and relay (i.e., transmit) this data to the remote computer 230 for analysis.

For purposes of discussion herein, the internal components of the hoof sensors 220a-d are described in reference to a general sensor 220. It will be appreciated that many or all of the components may be equally applicable to the head sensor 222 as well. As shown, the sensor 220 is an active sensor having is own power source 260. Energy from the power source 260 is provided to a measurement assembly 262 that may include one or more sub-sensors 264, 266 for sensing one or more measurable parameters. The sensor further includes a transmitter 268 and antenna 270 for transmitting measured data to the transceiver module 224. In addition to the components shown in the sensor 220, it will be appreciated that the sensor 220 may further include a memory and/or microprocessor 272. Such a memory/microprocessor be preprogrammed firmware or a separate memory structure (e.g. EPROM memory) and a separate microprocessor. In one arrangement, the sensor 220 may be programmed by the end users (e.g., prior to application). This may allow, for example, the ability to provide identification information with measured data and/or upon receiving an identification interrogation signal. In the latter regard, the sensor 220 requires a receiver unit. Referring briefly to FIG. 4, it will be noted that the sensor 220 may be formed as a small integrated circuit that may be disposed in a casing 280. This casing 280 may be filled with potting material. Preferably, the casing 280 is small, about the size of a quarter or smaller such that it may be non-intrusively attached to, for example, the hooves of the horse.

As shown, the sensor 220 includes two sub-sensors, a motion sub-sensor 264 and a temperature sub-sensor 266. However, it will be appreciated that the sensor 220 may include only a single sub-sensor or a larger number of sub-sensors (i.e., more than two). Further, the sub sensors may measure parameters other than temperature and motion, as discussed herein. The temperature sub-sensor 266 is operative, in response to an applied voltage, to produce an output indicative of a temperature of a portion of the sensor 220. In one embodiment, a thermally sensitive element (e.g., a thermistor or thermocouple) is utilized to provide a temperature signal that varies in a known manner with temperature. The temperature signal generated by the temperature sub-sensor 266 is then transmitted to the transceiver module 224.

In one embodiment, the motion sub-sensor 264 is an accelerometer. The accelerometer is operative to measure acceleration and vibration. The accelerometer may be one of a number of acceptable accelerometer types. Such types include, without limitation, piezoelectric, capacitance, null-balance, strain gage, resonance, piezoresistive and magnetic induction. These types of accelerometer may have from one axis to three axes of measurement, the multiple axes typically being orthogonal to each other.

Three main features may be considered when selecting accelerometers: amplitude range, frequency range, and ambient conditions. Acceleration amplitude range is measured in Gs, whereas frequency is measured in Hz. For use in a given environment, ambient conditions such as temperature may be considered as well as the maximum shock and vibration the accelerometers will be able to handle. The latter is the rating of how much abuse the accelerometer can withstand prior to failure and is different from how much vibration and/or acceleration an accelerometer can measure. Electrical output options depend on the system being used with the accelerometers. Common analog options are voltage, current or frequency. Digital output choices are also available.

For application as hoof sensors 220a-d, it will be appreciated that any component of the sensor 220 may be subject to high dynamic shock loading (i.e., G forces). For instance, when a steel shod horse trots on a solid surface (e.g., concrete) it has been determined that a mean hoof shock value of 96 Gs may be present upon initial impact. It is believed that hoof shock forces may, in extreme conditions, approach 300-400 Gs. Accordingly, the sensor components must be adapted to withstand a high shock environment. In the illustrated embodiment, the accelerometer utilized may be, for example, a MEMs based accelerometer such as available from a number of manufacturers. Such accelerometers are compact, have low power requirements and have suitable robustness. One current design uses two Analog Devices ADXL 321 chips deployed to provide calibrated XYZ axis data.

Alternatively, the motion sub-sensor 264 may be an inertial gyro sensor. Inertial gyros are sensors used to measure angular rates and x, y & z linear acceleration. Up to three angular or rotary axes, as well as three linear axes, can be measured using inertial gyro sensors. The most critical rotary performance specifications for inertial gyros are rotary rate, measuring how fast a device turns, and rated acceleration for linear axes. Both rotary and linear axes have specifications for accuracy as a positive or negative percentage of the full scale of measurement, the bandwidth, bias stability and transverse sensitivity. Axis bandwidth is the frequency range over which the device meets its accuracy specifications. Bias stability is the accuracy over a given operating temperature range. Transverse sensitivity is the inertial gyro's sensitivity to a force that is orthogonal to the desired direction of measurement.

A number of technology options for angular measurement are available. Inertial gyros with a gyro reference have an inertial mass used as a reference for rotational movements. A vibrating tuning fork or plates measure Coriolis force in inertial gyros made using MEMS technology. Gravity reference sensors, another technology and also known as inclinometers, cannot be used in gravity-free environments. Fiber optics is a unique way to measure angular displacement without moving parts. Linear acceleration technologies for inertial gyros are also numerous. For piezoelectric devices, a piezoelectric material is compressed by the proof mass and generates a charge that is measured by a charge amplifier. For strain gage devices, strain gages (strain-sensitive variable resistors) are bonded to parts of the structure that support the proof mass. These strain gages are typically used as elements in a Wheatstone bridge circuit, which is used to make the measurement. Capacitance-based accelerometers measure the variable capacitance between the support structure and the proof mass. The variable gap between the two is measured in a capacitance measurement circuit.

Electrical output options depend on the system being used with the inertial gyros. Common analog output options are voltage, current or frequency. Digital output choices are the standard parallel and serial signals. Of course use of digital outputs will require incorporation of a D/A converter in the sensor 220 prior to transmission. Another option is to use inertial gyros with an output of a change in state of switches or alarms. In addition, these sensors can have a vertical or artificial horizon output.

In the present embodiment, the inertial gyro sensor utilized may be a MEMs based gyroscope such as manufactured by Analog Devices (e.g., model ADIS 16100). Again, such devices are compact and have suitable robustness and other characteristics. It will be appreciated that both an accelerometer and an inertial gyro sensor may be incorporated into a single sensor 220.

Figure 5:
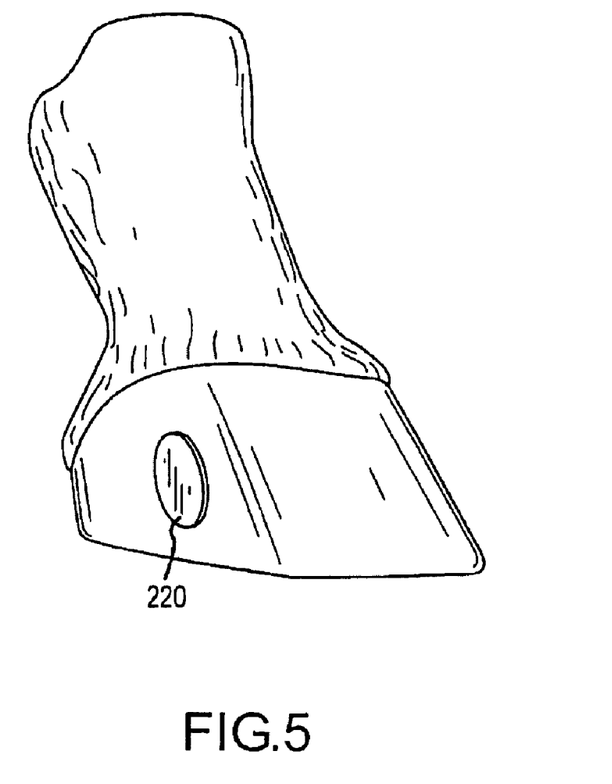
FIG. 5 illustrates a sensor attached to the hoof of an animal in accordance with the present invention.
Figure 6:
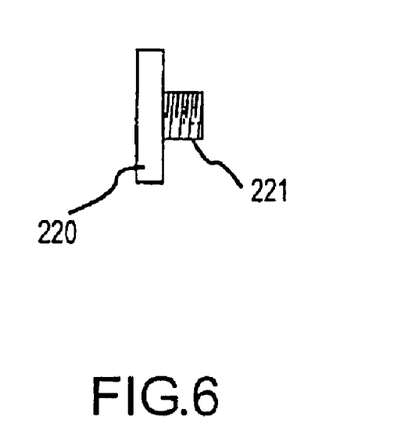
FIG. 6 is a side view of the sensor of FIG. 5.

FIG. 5 illustrates the interconnection of the sensor 220 to the hoof of a horse. As shown, the sensor 220 is adapted to be attached to the outside surface of the hoof. In one embodiment, the sensor 220 has an engagement surface it may be contoured to fit the curvature of the hoof. In such an arrangement, the sensor 220 may be adhered directly to the surface of the hoof. In another or complementary arrangement, the sensor 220 may include a threaded engagement tap 221. See FIG. 6. This threaded engagement tap 221 may be a simple screw that allows the sensor 220 to be threaded part way into the outer hard surface of the hoof. In another embodiment, the threaded engagement tap 221 includes a hollow center that allows the sensor 220 to blood and/or tissue beneath the hoof. In this latter embodiment, numerous additional sub-sensors may be included in the sensor to provide additional information regarding the horse.

Power Supply

The power supply 260 may be any device that permits the sensors 220, 222 to provide monitored data (e.g., motion data, temperature data, sound, etc.) at a predetermined rate for a predetermined period of time. In one arrangement, the power supply 260 may be a passive device such as a battery. Such a battery may be fully disposed within the casing 280 of the sensor 220, or, the battery may be external to the casing 280. For instance, the battery may be formed as thin, flat, flexible devices that allow for conformance and adherence to the hoof of a horse or other animal. Use of such an external battery may increase the life of the sensor 220. In another arrangement, the power supply may be a rechargeable power supply. In this regard, the power supply 260 may include a battery and rectifying circuitry that allows the battery to be recharged when the batteries is disposed within range of an appropriate radio frequency and/or magnetic induction charger. Such a charger may be included in, for example, a horse's stall such that the sensors may be charged overnight. In further arrangements of the power supply 260, active power supplies may be utilized. Such active power supplies may provide energy from thermoelectric conversion, kinetic energy and/or solar energy. As will be appreciated, different sensors may utilize different power sources. For instance, head or body mounted sensors may be better positioned to utilize solar energy whereas hoof/leg mounted sensors may more effectively utilize batteries, thermoelectric sources and/or kinetic sources.

Remote Computer/Processing

Figure 7:
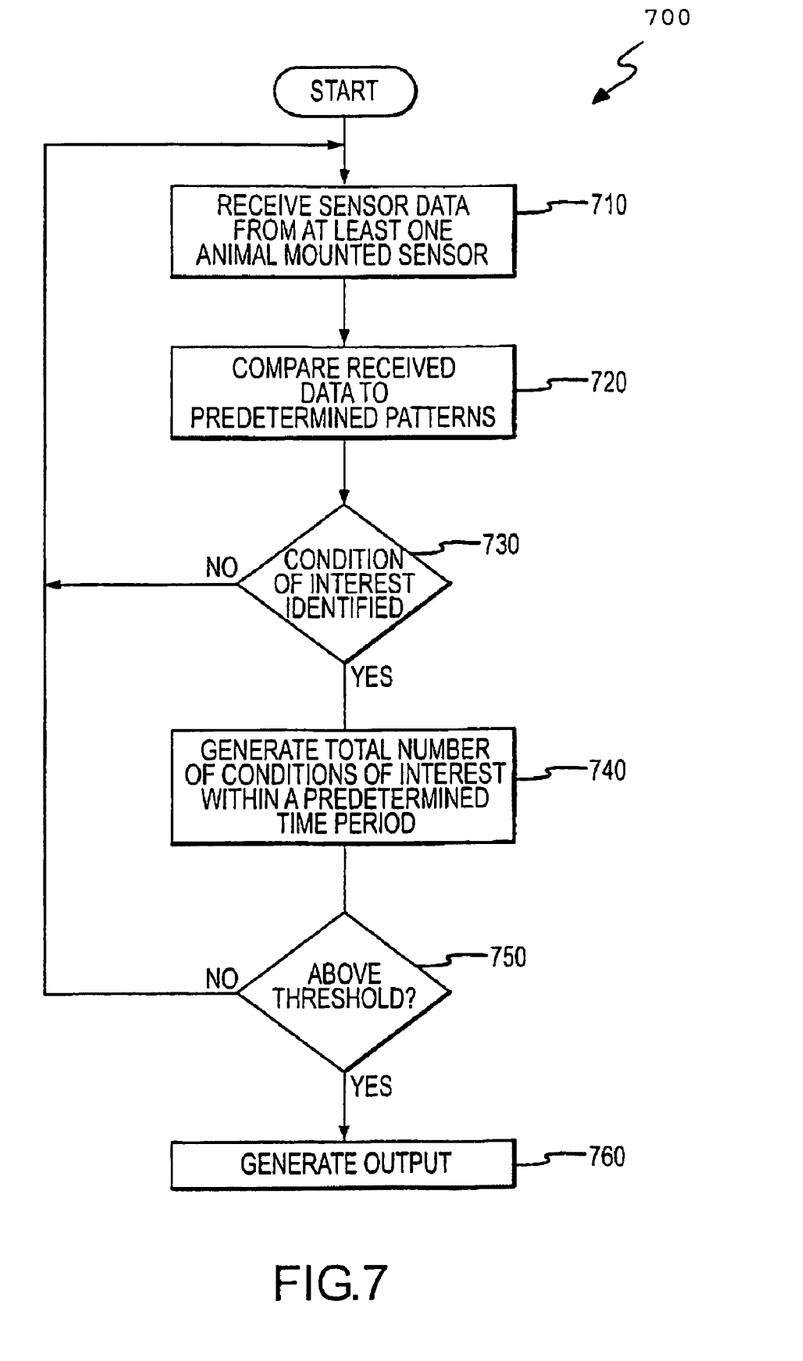
FIG. 7 is a flow chart illustrating a processing method in accordance with the present invention.

The remote computer 230, may utilize any appropriate processing structure to analyze data received from the transceiver module 224. For many monitoring situations such as colic monitoring, identification of predetermined movement patterns may be helpful in identifying an event of interest. In such instances, the remote computer 230 may utilize heuristic and/or artificial intelligence processing schemes to identify patterns and/or compare received data with predetermined data corresponding to a known condition. FIG. 7 is a flow chart illustrating a process 700 that may be utilized in accordance with the present invention. As shown, the remote computer 230 may receive (710) sensor data from at least one animal mounted sensor. The received data may then be compared (720) with any of a number of predetermined patterns to identify a condition of interest. For instance, when monitoring colic, motion sensor data may be processed to determine a posture/movement of a horse indicating colic. Secondary data may be utilized as well. In this regard, additional data from the sensor(s) such as temperature and or sound may be utilized in conjunction with primary sensor data (e.g., motion data) to identify a condition of interest. A determination (730) is made regarding whether the received data correspond to a condition of interest. If not, monitoring continues. If a condition of interest is identified, a total number of conditions of interest and multivariate parameters of each condition within predetermined time periods is generated in (740). The total number and multivariate parameters of each condition of interest are compared (750) to threshold values. If the threshold values are below predetermined values, monitoring continues. If they are above such values, the remote computer 230 generates an output, for example, to a caregiver such that human monitoring and/or intervention may occur. As will be appreciated, multiple different conditions of interest may be monitored.

Figure 8:
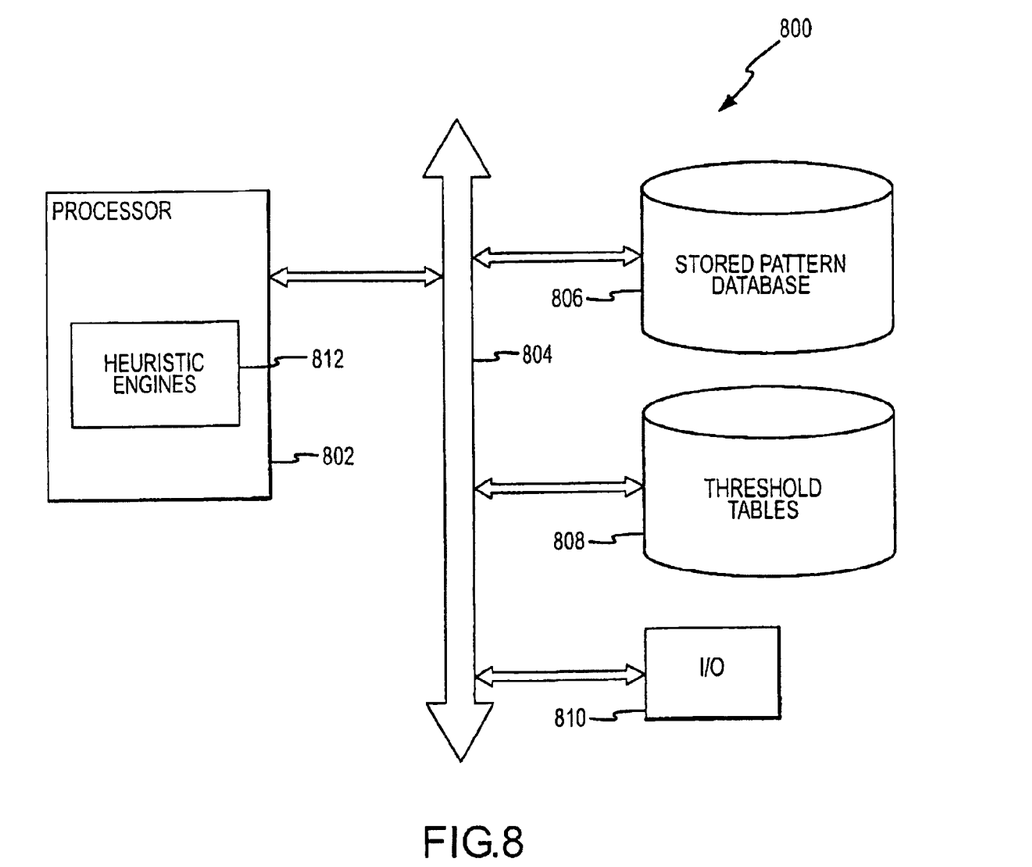
FIG. 8 is a schematic diagram of an animal monitoring system in accordance with the present invention.

FIG. 8 is schematic diagram illustrating an animal monitoring system in accordance with the present invention. Although the system 800 is illustrated as being implemented on a single processing platform, it will be appreciated that the associated functionality may be distributed over multiple platforms that may be interconnected via a LAN or a WAN. In the illustrated embodiment, the system 800 includes a processor 802, a stored pattern database 806, threshold tables 808 and input/output structure 810 all interconnected via a data bus. The processor 802 implements logic as discussed above for analyzing sensor signals to identify conditions or events of interest. In this regard, the processor 802 may access pattern information stored in the database 806. Such pattern information may identify baseline patterns (which may be particular to an individual animal) and patterns correlated to event indicators. For example, in the case of motion sensors used to detect colic, the pattern information may define signal characteristics correlated to characteristic colic motions.

The processor 802 further accesses threshold tables 808. The threshold tables may indicate amplitude, frequency, or other signal parameters and time parameters that distinguish artifact and baseline events from events of interest. The illustrated processor 802 further includes heuristic engines 812 used to identify events or conditions of interest. In this regard, the heuristic engines 812 may be provided with certain training data and then may develop over time to recognize baseline conditions and/or events of interest based on pattern learning logic. The processor 802 is operative to communicate with the sensor systems and with other platforms (for example, associated with experts use for analysis and/or owners or other caregivers) via the I/O structure 810.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed:

1. A method, comprising:

monitoring multiple horses in an animal husbandry setting to detect a colic related event by processing and analyzing data representing a plurality of postures and movements of each of said multiple horses, wherein said colic related event is associated with symptoms of abdominal pain represented by said plurality of postures and movements, said monitoring comprising the steps of:

providing sensor sets that detect motion related information to each of said multiple horses, wherein said motion related information comprises position, velocity, and acceleration representing said plurality of postures and movements, wherein said sensor set comprises a first motion sensor set comprising four sensors adhesively bonded to each hoof of each of said multiple horses and a second motion sensor removably disposed on a head of each of said multiple horses, and wherein said first motion sensor set and said second motion sensor comprise multi-axis accelerometers, inertial gyroscopic sensors, or combinations therof;

operating said sensor sets to provide data indicative of said motion related information;

outputting said data to a processor operably programmed with software for identifying said colic related event based on said data, wherein said outputting comprises using a wireless connection to transmit said data between said sensor sets and said processor;

receiving and processing said data in said software to create processed data that distinguishes portions of said data associated with different ones of said sensor sets associated with different ones of said multiple horses and to create processed data; and analyzing said processed data to identify said colic related event by comparing said processed data to stored pattern information comprising known baselines or thresholds, correlating said processed data to previously defined animal behaviors, utilizing pattern recognition algorithms on said processed data, or implementing a multi-variant analysis on the processed data.

* * * * *

UNITED STATES PATENT AND TRADEMARK OFFICE
CERTIFICATE OF CORRECTION

PATENT NO. : 7,335,168 B2
APPLICATION NO. : 11/198914
DATED : February 26, 2008
INVENTOR(S) : Rugg

It is certified that error appears in the above-identified patent and that said Letters Patent is hereby corrected as shown below:

Column 9, line 41, delete "mnacroenvironment" and insert therefor --macroenvironment--.

Column 18, line 34, delete "therof" and insert therefor --thereof--.

Signed and Sealed this

Twenty-ninth Day of July, 2008

JON W. DUDAS
*Director of the United States Patent and Trademark Office*